United States Patent [19]

Parizek

[11] Patent Number: 4,758,517
[45] Date of Patent: Jul. 19, 1988

[54] PROCESS FOR GROWTH OF TREPONEMA HYODYSENTERIAE

[75] Inventor: Richard E. Parizek, Lenexa, Kans.

[73] Assignee: Mobay Corporation, Pittsburg, Pa.

[21] Appl. No.: 923,852

[22] Filed: Oct. 28, 1986

Related U.S. Application Data

[63] Continuation-in-part of Ser. No. 732,872, May 10, 1985, abandoned.

[51] Int. Cl.$^4$ .................. C12N 1/20; C12N 1/38; C12R 1/01
[52] U.S. Cl. .................. 435/253; 435/244; 435/822
[58] Field of Search .......... 424/92, 101; 435/253, 435/244; 260/397.2, 397.25

[56] References Cited

U.S. PATENT DOCUMENTS

| | | | |
|---|---|---|---|
| 3,919,411 | 11/1975 | Glass et al. | 424/92 X |
| 4,100,272 | 7/1978 | Glock et al. | 424/92 |
| 4,152,413 | 5/1979 | Goodnow | 424/92 |
| 4,152,415 | 5/1979 | Harris et al. | 424/92 X |
| 4,203,968 | 5/1980 | Harris et al. | 424/92 |
| 4,290,774 | 9/1981 | Girgis et al. | 530/359 X |
| 4,469,672 | 9/1984 | Harris | 424/92 X |

OTHER PUBLICATIONS

Lemcke et al. "Sterol Requirement for the Growth of *Treponema hyodysenteriae*" J. Gen. Micro 116:539–543, 1980.

Washburn et al. "Mycoplasma growth factors in bovine serum fraction" J. Bacteriol 135:818–827, 1978.

*Primary Examiner*—Lionel M. Shapiro
*Attorney, Agent, or Firm*—Louis E. Davidson

[57] ABSTRACT

A process is provided for increasing the yield of active cells of *Treponema hyodysenteriae* by growing such cells in a nutrient medium containing a cholesterol-rich bovine fraction. Killed cells grown in this manner can be used to produce a bacterin which is effective against swine dysentery.

3 Claims, No Drawings

PROCESS FOR GROWTH OF TREPONEMA HYODYSENTERIAE

This is a continuation-in-part of U.S. application Ser. No. 732,872, filed May 10, 1985, now abandoned.

BACKGROUND AND PRIOR ART

Swine dysentery is a severe mucohaemorragic diarrhea primarily affecting pigs post weaning. Control of the disease has been generally accomplished through use of chemobiotics and antibiotics. To date, there has been no effective nondrug prophylactic agent to control this disease. The anaerobic spirochete, *Treponema hyodysenteriae*, is recognized to be the primary etiological agent of swing dysentery. U.S. Pat. No. 4,100,272 discloses the use of a vaccine or bacterin containing killed cells of *T.hyodysenteriae* to increase the resistance of swine to swine dysentery.

This prior art method has not resulted in commercial acceptance, because the bacterin product has relatively low activity. The described treatment schedule includes six intravenous injections. It is desired to have a bacterin that can be used in a treatment schedule involving fewer intramuscular injections.

Cholesterol-rich fractions are known to be useful as growth promoters for some organisms. J.Bacteriol., Vol. 135, No. 3, pp. 818–827 (1978) describes the use of a cholesterol-rich fraction as a growth promoter for *Mycoplasma pneumoniae* and *Mycoplasma arthritidis*. J.Gen.Microbiology, Vol. 116, pp. 539–543 (1980) describes the use of USP cholesterol in the growth of *T.hyodysenteriae*.

There is no known prior art that suggests the specific use of cholesterol-rich bovine fractions to enhance the yield of cells of *T.hyodysenteriae* for subsequent inclusion in a bacterin suitable for control of swine dysentery.

SUMMARY OF THE INVENTION

In accordance with the present invention, a process is provided for the growth of *Treponema hyodysenteriae* in an appropriate nutrient medium for subsequent use of the resulting cells in a bacterin, wherein the nutrient medium contains a cholesterol-rich bovine fraction.

DESCRIPTION OF THE INVENTION

The process of the present invention can be practiced with any virulent strain of *T.hyodysenteriae*. A virulent strain is one which is capable of producing a typical swine dysentery infection. Two particular strains (B204 and B234) have been found useful for this purpose. These have been deposited with the American Type Culture Collection and have designations ATCC No. 31212 (B204) and ATCC No. 31287 (B234).

The *T.hyodysenteriae* strain can be grown in media comprising a mixture of Tryptic Soy Broth (Difco Laboratories) supplemented with fetal calf serum or lamb serum, dextrose, 1-cysteine HCl, vitamin B-12, and yeast extract. The improvement of the present invention is including a cholesterol-rich bovine fraction in such media for growth of the *T.hyodysenteriae* cells. The cholesterol-rich bovine fraction is preferably present in an amount of 1.0 to 2.5 volume percent based upon the volume of the media, but it can be used in an amount from 0.1 to 5.0 volume percent.

Cholesterol-rich bovine fractions suitable for use in the process of this invention are available from several sources. Cholesterol Concentrate Code 82-010 available from Miles Scientific Division of Miles Laboratories, Inc. and prepared from bovine serum according to the process disclosed and claimed in U.S. Pat. No. 4,290,774 is useful. Bovine Cholesterol Concentrate List 3200 available from Biocell Laboratories is another useful material. The preferred cholesterol-rich bovine fraction useful in the process of this invention is prepared by a process comprising the steps of:

(a) contacting a liquid cholesterol-containing bovine plasma or serum or fraction thereof with a silica adsorbent to adsorb the cholesterol-rich fraction;

(b) separating the adsorbed cholesterol-rich fraction from the remaining liquid plasma or serum;

(c) freezing and thawing the adsorbed cholesterol-rich fraction;

(d) eluting the adsorbed cholesterol-rich fraction at a pH from 9.0 to 11.5;

(e) either before or after step (f) and prior to step (g) adjusting the pH of the cholesterol-rich solution to a value in the range from 11.0 to 13.0;

(f) concentrating the cholesterol-rich solution by ultrafiltration;

(g) dialyzing the concentrated cholesterol-rich solution sequentially against sodium carbonate and water;

(h) further concentrating the dialyzed cholesterol solution by ultrafiltration;

(i) adjusting the pH of the concentrated cholesterol-rich solution to a value in the range from 7.0 to 11.0;

(j) heating the concentrated cholesterol-rich solution at 50° to 100° C. for 30 minutes to 24 hours; and (k) recovering therefrom a purified cholesterol-rich bovine fraction.

This specific fraction and its production process are described and claimed in copending U.S. application Ser. No. 923,850 filed concurrently herewith.

The starting material for use in the production of the cholesterol-rich fraction can be any bovine blood plasma or serum or fraction thereof containing cholesterol. The preferred starting material is bovine serum. If the starting material is serum, it is preferred to add a soluble salt, such as sodium citrate, to an ionic strength of 0.25 to 1.0. Other suitable salts include sodium chloride, sodium phosphate, potassium phosphate, ammonium sulfate and sodium sulfate. The addition of a soluble salt to the above concentration will increase the amount of cholesterol adsorbed in the subsequent silica adsorption step. Bovine plasma is normally collected by a method which includes addition of citrate as an anticoagulant. This salt concentration is usually sufficient for the adsorption step and no additional salt is needed.

The plasma or serum starting material is maintained at a temperature of from 0° C. to 50° C. preferably from 20° C. to 25° C. The pH is adjusted to a range of from 5.5 to 9.0, preferably from 7.0 to 8.0.

The silica adsorbent useful in this invention does not have a critical composition. Appropriate silica materials are the microfine silica available under the trademark Cabosil from Cabot Corporation and the powdered silica available under the trademark Aerosil 380 from Cary Company. The silica is added to the liquid plasma or serum in an amount of 1 to 50 g/l., preferably from 10 to 20 g/l. The silica suspension in the liquid plasma or serum is then mixed for about 3 to 4 hours. It is preferred to add to the silica suspension about 10 g/l of a polyethylene glycol having a nominal molecular weight of about 3350 daltons. A suitable material is Union Carbide Corporation Carbowax PEG 3350. The polyethylene glycol aids in the subsequent separation of the silica.

The silica containing adsorbed cholesterol-rich fraction is then separated from the remaining liquid plasma or serum preferably by centrifugation, and the liquid phase is discarded. The silica paste is then frozen at −20° C. and held at this temperature for at least one week and preferably two weeks. The frozen paste is then thawed to room temperature (about 20°–25° C.) for 24 to 48 hours until no visible ice crystals are present. Any liquid that is expressed from the thawed paste is discarded.

The silica paste is washed to remove any undesirable proteins. This is accomplished by suspending the paste in an aqueous salt solution containing about 0.15 M sodium chloride. Other useful salts are sodium acetate and sodium phosphate. The salt solution is used in an amount about 2 liters for each kilogram of the paste. The paste is separated from the liquid. This washing procedure using a salt solution is preferably repeated at least two times to remove occluded proteins.

The washed paste is suspended in about 2 liters of deionized or distilled water per kilogram of paste, and the pH is adjusted to 9.0 to 11.5, preferably 10.4 to 10.6, by the addition of appropriate amounts of sodium hydroxide or hydrochloric acid. The suspension is stirred for about 2 hours during which time the pH is maintained at the desired level by periodic additions of the above alkaline or acid material. This treatment elutes the desired cholesterol-rich fraction from the silica. The suspension is then allowed to settle for 12 to 24 hours, preferably 12–18 hours. The supernatant containing the cholesterol-rich fraction is siphoned off for further treatment. It is preferred to use only this first elution for production of the desired cholesterol-rich fraction product. However, it is possible to repeat the above alkaline suspension, elution, stirring and settling steps two more times and pool the supernatants from the second and third elutions with the first elution material. The silica is discarded.

The cholesterol-rich solution is clarified by filtration and centrifugation to remove any traces of silica and then preferably frozen at −20° C. and stored at that temperature for 48–72 hours. The frozen material is then thawed at room temperature for at least 24–48 hours until no visible ice crystals are present. The resulting liquid product is clarified by centrifugation and any solid material is discarded. This freeze-thaw cycle assists in removal of silica which otherwise interferes with subsequent processing steps. The clarified liquid is then concentrated to 15 to 50 percent, preferably 20 to 25 percent, of its initial volume, by ultrafiltration techniques.

The concentrated cholesterol-rich solution is then dialyzed against an alkaline material, such as aqueous sodium carbonate, to further remove silica. In order to improve the effectiveness of this dialysis step, it is desirable for the cholesterol-rich solution to be at pH 11.0 to 13.0, preferably pH 12.0. The pH can be adjusted to this value by alkaline addition. This can take place just prior to the dialysis step, but it is preferred for operating convenience to adjust the pH to this value before the cholesterol-rich solution is subjected to the above-discussed ultrafiltration concentration step.

In the dialysis step, the cholesterol-rich solution is dialyzed against 6–7 volumes of 0.01–0.3 M sodium carbonate to remove silica followed by dialysis against 6–7 volumes of deionized water to remove the sodium carbonate. The resulting solution is then concentrated by ultrafiltration to its volume prior to dialysis.

The pH of the concentrated cholesterol-rich solution is then adjusted to a value in the range from 7.0 to 11.0, preferably pH 8.6.

The concentrated cholesterol-rich solution is heated to 50° to 100° C., preferably 80° C., for 30 minutes to 24 hours, preferably 30 minutes to 5 hours, in order to increase the storage stability of the cholesterol-rich fraction. The solution is then cooled to about 30° C. It is convenient for handling purposes that the desired product contain about 0.50 to 30 mg./ml, preferably 10 to 20 mg./ml, of cholesterol. It is preferred to analyze the above cooled product for cholesterol using known techniques and to dilute the product with deionized water to the desired concentration.

While it is not necessary in the process for production of the cholesterol-rich fraction, it is convenient that the product contain about 8.5 g/l sodium chloride and have a pH adjusted to 7.7–7.9 so that it is generally compatible with media employed for cell culture. The product is then sterile filtered to recover a purified cholesterol-rich fraction. This product is not pure cholesterol, but it is mixed with minor amounts of unidentified materials which passed through the production process.

Pure cholesterol is not suitable for use in this invention since it does not appreciably affect the growth of *T.hyodysenteriae* in the way achieved by the cholesterol-rich bovine fractions.

The *T.hyodysenteriae* cells are grown in the media containing the cholesterol-rich bovine fraction under conditions well-known to those skilled in the art. The resulting cells are then killed in a well-known manner by using agents, such as formalin, merthiolate, or beta-propiolactone. The cells are then harvested and suspended in an appropriate carrier medium to produce a desired bacterin.

The activity of the bacterin can be further enhanced by the use of an adjuvant. An adjuvant that is preferred for use with the *T.hyodysenteriae* cells produced by the process of the present invention is the combination of an acrylic acid polymer cross-linked with a polyallyl saccharide and a specific emulsion system disclosed and claimed in U.S. Pat. No. 3,919,411. Such adjuvant is marketed by the Bayvet Division of Mobay Corporation under the trademark HAVLOGEN.

It has been found that the *T.hyodysenteriae* bacterin produced in the above manner can be injected intramuscularly in only two doses at three week intervals to significantly increase the resistance of pigs to swine dysentery.

The invention will be further described in the following examples.

EXAMPLE 1

Cholesterol-rich bovine fraction was prepared in the following manner. Fresh bovine serum was brought to a temperature of 20°-25° C. and 14.7 g/l of sodium citrate (serum ionic strength of 0.5) was added. The resulting solution was agitated for 30 minutes, and the pH was adjusted to 7.0 by addition of an appropriate amount of 1N sodium hydroxide. Finely-divided silica was added in an amount of 10 g/l and the resulting slurry was agitated for 3 hours at room temperature. The silica containing adsorbed material was then separated from the liquid phase by centrifugation, and the liquid was discarded. The silica paste was then frozen at −20° C. and stored at that temperature for 2 weeks. The frozen paste was then thawed at room temperature for 48 hours. The expressed liquid was discarded. The silica paste was then suspended in 2 liters of 0.85 percent (weight/volume basis) aqueous sodium chloride solution (0.146M NaCl) for each kilogram of silica paste. It was mixed gently for 15 minutes and allowed to settle for at least 3 hours. The supernatant liquid was siphoned off and discarded. This washing step was repeated two times. The washed paste was then suspended in 2 liters of deionized water per kilogram of silica paste with agitation at room temperature. The resulting suspension was then carefully warmed to 20°–25° C. The pH was adjusted to 10.5 with addition of 1N sodium hydroxide. The resulting suspension was stirred at room temperature for 2 hours while readjusting pH to 10.5. The stirring was stopped, and the suspension was allowed to settle for 18 hours. The supernatant was removed by siphon and clarified by filtration and centrifugation. The silica was discarded. The clarified solution was then concentrated to 20 percent of its initial volume by ultrafiltration. The pH of the concentrated material was adjusted to 11.2 by addition of 1N sodium hydroxide. The concentrated material was then dialyzed against 6 volumes of 0.01M sodium carbonate at pH 11.2. It was then dialyzed against 6 volumes of deionized water. The cholesterol level of the concentrate was analyzed by known techniques and further concentrated by ultrafiltration to a cholesterol level of 10 mg./ml. The pH was then adjusted to 7.6 by addition of 1N hydrochloric acid, and the resulting solution was heated at 80° C. for 1 hour. The solution was then cooled to room temperature. Sodium chloride was added in an amount of 8.5 g/l and the resulting solution was sterile filtered. The filtered material was then recovered as a purified cholesterol-rich bovine fraction.

Frozen seed of *T.hyodysenteriae* strain ATCC No. 31212 was inoculated into a glass tube containing 13 ml. of Tryptic Soy Broth (Difco Laboratories,, 27.5 g/l), 10 percent fetal calf serum, 0.5 percent dextrose, 0.05 percent 1-cysteine HCl and 0.25 mcg/ml vitamin B-12. Such percents were on a weight/volume basis. The tube was then sealed and incubated under an anaerobic atmosphere containing 10 volume percent hydrogen, 80 volume percent nitrogen, 10 volume percent carbon dioxide at 37° C. for 72 hours. The resulting seed culture was then passaged to 2 tubes containing the same media which were incubated at 37° C. for 24 hours under the same conditions. The contents of the tubes were pooled. A 7 ml portion of the pooled active seed culture was then added to each of two 500 ml. bottles each containing 200 ml. of Tryptic Soy Broth, 1 percent yeast extract, 5 percent lamb serum, 0.5 percent dextrose, 0.05 percent 1cysteine HCl and 0.25 mcg/ml. vitamin B-12. Such percents were on a weight/volume basis. The bottle contents were then incubated under the above-described anaerobic atmosphere at 37° C. until turbid (about 24 hours).

The resulting expanded seed cultures were then divided into two portions, and each portion was used alone to inoculate one of two 14 liter pilot fermenters each containing 7 liters of Tryptic Soy Broth, 1 percent yeast extract, 3 percent lamb serum, 1 percent dextrose, 0.05 percent 1-cysteine HCl and 0.25 mcg/ml. vitamin B-12. Such percents were on a weight/volume basis. One of the fermenters was further supplemented with 2.5 volume percent of the cholesterol-rich bovine fraction prepared as described above. Both fermenters were then incubated at 37° C. for 44 hours under the above anaerobic atmosphere. The pH was controlled at 6.5 by periodic additions of 5N sodium hydroxide.

At the conclusion of the above incubation, appropriate samples were taken from each fermenter, and the fermenter contents were then treated with 0.15 volume percent formalin to inactivate the cells. The cell samples were examined microscopically, the total cell count was measured in a Petroff-Hauser counting chamber, and the viable cell count was determined by serial dilution on freshly poured 5 percent bovine blood agar plates. The blood agar plates were incubated at 37° C. under an anaerobic atmosphere of 50 volume percent hydrogen and 50 volume percent carbon dioxide for 4 days. The *T.hyodysenteriae* colonies were observed as individual zones of hemolysis. The results of these examinations are listed below in Table 1.

TABLE 1

Growth of *T. hyodysenteriae* ATCC 31212 in Media With and Without Cholesterol-Rich Bovine Fraction

| Media | Microscopic Examination | Total Cell Count | Viable Cell Count |
|---|---|---|---|
| Without Cholesterol Fraction | Loosely coiled; relatively long thin walled cells; generally inactive | $1.3 \times 10^9$/ml | $3.7 \times 10^7$/ml |
| With Cholesterol Fraction | Tightly coiled; shorter, thicker walled cells; active | $2.6 \times 10^9$/ml | $1.4 \times 10^9$/ml |

It can be seen from the above data that the presence of the cholesterol-rich bovine fraction doubled the total cell count, increased viable cell count 100-fold, and had a positive effect on cell morphology.

EXAMPLE 2

Seed cultures of *T.hyodysenteriae* ATCC No. 31212 prepared as described in Example 1 above were then used to inoculate at a 3 volume percent level the contents of three 500 ml. bottles each containing 200 ml. of Tryptic Soy Broth mixed with 1 percent yeast extract, 3 percent lamb serum, 1 percent dextrose, 0.05 percent 1-cysteine HCl and 0.25 mcg/ml. vitamin B-12. The percents were on a weight/volume basis. One of the bottles (Control) contained 2.5 volume percent of the cholesterol-rich bovine fraction prepared as described in Example 1. A second bottle contained 2.5 volume percent of Cholesterol Concentrate Code 82-010 from Miles Laboratories, Inc. A third bottle contained 2.5 volume percent Bovine Cholesterol Concentrate List 3200 from Biocell Laboratories. These inoculated bottles were then incubated under an anaerobic atmosphere of 10 volume percent hydrogen, 80 volume percent nitrogen and 10 volume percent carbon dioxide at 37° C. for 38 hours. The bottle contents were adjusted to pH 7.0 at 24 and 31 hours by addition of 2N sodium hydroxide. The total cell count from each bottle was measured in a Petroff-Hauser counting chamber. The results are shown below in Table 2.

TABLE 2

Growth of *T. hyodysenteriae* ATCC No. 31212 in Media Containing Various Cholesterol-Rich Bovine Fractions

| Media Supplement | Total Cell Count |
|---|---|
| Preferred cholesterol fraction (Control) | $2.5 \times 10^9$/ml |

TABLE 2-continued Growth of T. hyodysenteriae ATCC No. 31212 in Media Containing Various Cholesterol-Rich Bovine Fractions

| Media Supplement | Total Cell Count |
| --- | --- |
| Cholesterol Concentrate Code 82-010 | $2.7 \times 10^9$/ml |
| Bovine Cholesterol Concentrate List 3200 | $3.0 \times 10^9$/ml |

It can be seen from the above data that cholesterol-rich bovine fractions from various sources can be employed to produce a desirably high cell count of T.hyodysenteriae.

EXAMPLE 3

The procedure of Example 1 was generally repeated using T.hyodysenteriae strain ATCC No. 31287 with media supplemented with the preferred cholesterol-rich fraction to produce a high concentration of cells.

EXAMPLE 4

A vaccine or bacterin was prepared by mixing the killed T.hyodysenteriae cells prepared in the manner described in Example 1 using the preferred cholesterol-rich fraction in the growth media with 10 volume percent HAVLOGEN adjuvant described in U.S. Pat. Nos. 3,919,411 and 1:10,000 merthiolate. The vaccine contained $2 \times 10^9$ cells/ml. This vaccine was then used in five separate challenge studies to determine the effectiveness of the vaccine against swine dysentery. In each of the vaccination/challenge studies the swine were obtained from a herd with no history of swine dysentery and were of mixed sex and generally Yorkshire, Hampshire or Cross breeds. At the time of first vaccination, the swine were at least 3 weeks post weaning and in the range of 35 to 40 lbs.

All vaccination/challenge studies were run in an isolation facility permitting segregation of vaccinated and control swine. The pigs were fed a protein grower ration containing no antibiotics. Prior to challenge, the swine were rectal swabbed and shown to be free of T.hyodysenteriae and Salmonella spp. following testing on appropriate isolation media.

The swine were challenged intragastrically with T.hyodysenteriae strains ATCC No. 31212 or 31287 which had been grown by a procedure similar to Example 1 except that the final cells were not killed. The challenge dose consisted of 100 ml. of active culture diluted to contain $10^8$ to $10^9$ organisms which was administered to individual pigs via stomach tube, following a 48 hour starvation period.

Each challenged pig was observed on a daily basis over a 28 day post challenge observation period. Following onset of clinical disease, dysenteric pigs were rectal swabbed to isolate the causative agent. Confirmation of T.hyodysenteriae infection was made by subculturing swabs onto Spectinomycin blood agar plates, incubating at 42° C. for 4 to 6 days, and microscopically examining hemolytic agar plaques for presence of spirochetes. A necropsy was performed on each pig which died during the five studies. Macroscopic lesions were recorded, and rectal swabs were taken of colonic mucosa to be subcultured as above.

Clinical response of individual swine to challenge was measured using the following Clinical Index:

| CLINICAL INDEX | | |
| --- | --- | --- |
| General Condition | Feces Composition | Feces Consistency |
| 0 - Normal | 0 - Normal | 0 - Normal |
| 1 - Diarrhea | 1 - Mucus | 1 - Soft |
| 2 - Dysentery | 2 - Blood & Mucus | 1.5 - Loose |
| 3 - Gaunt | 3 - Blood | 2 - Runny |
| 4 - Moribund | | 3 - Watery |
| 5 - Dead | | |

Various methods of analysis were used to evaluate clinical index data and are defined below:

(a) Daily Clinical Index (DCI)—A daily clinical index for each challenged pig was calculated using the three above described parameters:
DCI=General condition+Feces Composition+Feces Consistency (b) Daily Group Clinical Index (DGCI)—A daily group clinical index for vaccinate and control groups was calculated using the following formula:

$$DGCI = \frac{\Sigma DCI\text{'s (for all pigs in a group)}}{\text{Number of pigs in a group}} \times 100$$

(c) Individual Cumulative Clinical Index (ICCI)—A cumulative clinical index for each pig over the entire 28 day post-challenge period was calculated as follows:

$$ICCI = \frac{\Sigma DCI\text{'s (for 28 days post-challenge)}}{\text{Total number of observations (84)}} \times 100$$

(d) Group Cumulative Clinical Index (GCCI)—A group cumulative clinical index for vaccinates and controls was obtained by averaging the ICCI's within a particular group of pigs:

$$GCCI = \frac{\Sigma ICCI\text{'s (for all pigs in a group)}}{\text{Number of pigs in a group}}$$

Study No. 1: Ten (10) pigs were divided equally into two rooms. Five vaccinates received two 5 ml. intramuscular doses of the above described vaccine at three week intervals. Five unvaccinated control pigs were held in a separate room. Two weeks post booster, all pigs were challenged with virulent T.hyodysenteriae ATCC No. 31212.

Study No. 2: Twenty-nine (29) pigs were divided into 5 rooms of 23 vaccinates and two rooms of 6 controls. Vaccinates received two 5 ml. intramuscular doses of the above described bacterin at three week intervals. Challenge was the same as in Study No. 1.

Study No. 3: Ten (10) pigs were divided equally into two rooms. Five vaccinates received two 5 ml. intramuscular doses of the above-described bacterin at three week intervals. Five pigs were held as unvaccinated controls. Two weeks post booster all pigs were challenged with virulent T.hyodysenteriae ATCC No. 31287.

Study No. 4: Forty-six (46) pigs were divided into nine rooms of 36 vaccinates and two rooms of 10 unvaccinated controls. Vaccinated swine received two 4 ml. doses of the above described bacterin at three week intervals. Challenge was the same as in Study No. 3.

Study No. 5: Forty-six (46) pigs were divided into nine rooms of 36 vaccinates and two rooms of 10 unvaccinated controls. Vaccinated swine received two 5 ml. doses of the above described bacterin at three week intervals. Challenge was the same as in Study No. 1.

The five studies included a total of 105 vaccinates and 36 controls. Results of the five studies are summarized in Tables 3 and 4.

pigs died post-challenge (13.3%). Onset of clinical dysentery was significantly delayed and duration of clinical disease reduced in vaccinated swine.

Confirmation of *T. hyodysenteriae* as the causative agent of clinical dysentery was achieved in all cases following plating of rectal swabs on spectinomycin blood agar plates. Simultaneous plating on selective media for Salmonella spp. gave negative results.

Colonic contents of dead pigs were bloody and wa-

TABLE 3

CLINICAL RESPONSE OF PIGS CHALLENGED INTRAGASTRICALLY WITH *T. HYODYSENTERIAE* ATCC NO. 31212

| | No. of Pigs | Clinical Dysentery | | | | Gaunt | | Death | | | Group Clinical Index |
|---|---|---|---|---|---|---|---|---|---|---|---|
| | | No. of Cases | Percent | Mean Day Onset | Mean Days Duration | No. of Cases | Percent | No. of Cases | Percent | Days Anorexia | |
| VACCINATES | | | | | | | | | | | |
| Study 1 | 5 | 1 | 20 | 10 | 5 | 0 | 0 | 0 | 0 | 0 | 8.8 |
| Study 2 | 23 | 8 | 34.7 | 12.6 | 3.5 | 1 | 4.3 | 0 | 0 | 1 | 23.3 |
| Study 5 | 36 | 2 | 5.5 | 15.5 | 3.5 | 0 | 0 | 0 | 0 | 0 | 2.3 |
| TOTAL | 64 | 11 | 17.2 | 12.9 | 3.6 | 1 | 1.6 | 0 | 0 | 1 | 10.4 |
| CONTROLS | | | | | | | | | | | |
| Study 1 | 5 | 5 | 100 | 10.8 | 12.9 | 0 | 0 | 3 | 60 | 9 | 159.0 |
| Study 2 | 6 | 4 | 66.7 | 7.0 | 8.4 | 0 | 0 | 1 | 16.7 | 4 | 82.3 |
| Study 5 | 10 | 6 | 60 | 10.3 | 6.6 | 1 | 10 | 1 | 10 | 2 | 45.9 |
| TOTAL | 21 | 15 | 71.4 | 9.6 | 10.3 | 1 | 4.8 | 5 | 23.8 | 15 | 83.2 |

Following intragastric challenge with strain ATCC 31212, clinical dysentery was observed in 17.2% of vaccinated pigs (11 of 64) and in 71.4% of control pigs (15 of 21). This represents a 75.9% reduction in actual cases of clinical dysentery among vaccinated pigs. The cumulative clinical index (GCCI) calculated for the entire 28 day post-challenge observation period was 10.4 for vaccinated pigs as compared to 83.2 for unvaccinated controls. This represents an 87.5% reduction in total clinical signs (diarrhea, dysentery, gauntness, death) as measured by the clinical index. No deaths were seen among vaccinated pigs whereas 5 of 21 control pigs dies post challenge (23.8%). Onset of clinical dysentery was delayed in vaccinated pigs and duration of clinical disease reduced. Anorexia was appreciably reduced in vaccinated swine.

tery, and the colons themselves were grossly inflamed and devoid of villi. Rectal swabs taken from intestinal walls at time of necropsy were positive for *T. hyodysenteriae* and negative for Salmonella spp. Rectal swabs taken from protected vaccinates at 28 days post challenge were negative in all cases following subculture on spectinomycin blood agar plates at 42° C.

Taking all 141 vaccinated and control pigs into account, one can construct Table 5 summarizing clinical response through five challenge studies. Of 105 vaccinates, 25.5 developed clinical dysentery (24.3%) whereas 25.5 of 36 unvaccinated controls developed clinical dysentery (70.8%). This represents a 65.7% reduction in clinical dysentery among all vaccinated swine. Seven of 36 control pigs died post challenge (19.4%) whereas no vaccinated swine died post chal-

TABLE 4

CLINICAL RESPONSE OF PIGS CHALLENGED INTRAGASTRICALLY WITH *T. HYODYSENTERIAE* ATCC No. 31287

| | No. of Pigs | Clinical Dysentery | | | | Gaunt | | Death | | | Group Clinical Index |
|---|---|---|---|---|---|---|---|---|---|---|---|
| | | No. of Cases | Percent | Mean Day Onset | Mean Days Duration | No. of Cases | Percent | No. of Cases | Percent | Days Anorexia | |
| VACCINATES | | | | | | | | | | | |
| Study 3 | 5 | 2 | 40 | 11.5 | 3.0 | 0 | 0 | 0 | 0 | 0 | 21.2 |
| Study 4 | 36 | 12.5 | 34.7 | 13.6 | 2.5 | 0 | 0 | 0 | 0 | 0 | 18.2 |
| TOTAL | 41 | 14.5 | 35.4 | 13.3 | 2.6 | 0 | 0 | 0 | 0 | 0 | 18.6 |
| CONTROLS | | | | | | | | | | | |
| Study 3 | 5 | 3 | 60 | 6.3 | 15.3 | 1 | 20 | 1 | 20 | 4 | 93.2 |
| Study 4 | 10 | 7.5 | 75 | 6.6 | 6.4 | 1 | 10 | 1 | 10 | 0 | 63.6 |
| TOTAL | 15 | 10.5 | 70 | 6.6 | 8.9 | 2 | 13.3 | 2 | 13.3 | 4 | 73.5 |

Following intragastric challenge with strain ATCC 31287 clinical dysentery was observed in 35.4% of vaccinated pigs (14 of 41, one pig ±) and in 70.0% of control pigs (10 of 15, one pig ±). This represents a 49.4% reduction in actual cases of dysentery among vaccinated swine. The group cumulative clinical index for vaccinated pigs was 18.6 as compared with 73.5 for unvaccinated controls. This represents a 74.7% reduction in total clinical signs among vaccinates. No deaths were seen among vaccinates whereas 2 of 15 control lenge. The Group Cumulative Clinical Index for all 105 vaccinated pigs is 13.6; the G.C.C.I. for 36 unvaccinated controls is 79.2. This translates into an 82.8% reduction in total clinical signs (diarrhea, dysentery, gauntness, death) among all vaccinated pigs.

Taking Vaccination/Challenge results from the five individual studies into consideration, one can conclude that the *T. hyodysenteriae* bacterin will show a definite degree of efficacy when used under field conditions as an aid in prevention of Swine Dysentery.

TABLE 5

VACCINATION CHALLENGE STUDIES 1, 2, 3, 4, 5
CLINICAL RESPONSE OF PIGS CHALLENGED INTRAGASTRICALLY WITH
*TREPONEMA HYODYSENTERIAE* STRAINS ATCC No. 31212 and 31287

|  | No. of Pigs | Clinical Dysentery | | | | Gaunt | | Death | | Days Anorexia | Group Clinical Index |
|---|---|---|---|---|---|---|---|---|---|---|---|
|  |  | No. of Cases | Percent | Mean Day Onset | Mean Days Duration | No. of Cases | Percent | No. of Cases | Percent | | |
| Vaccinates | 105 | 25.5 | 24.3 | 13.1 | 2.8 | 1 | 1.0 | 0 | 0 | 1 | 13.6 |
| Controls | 36 | 25.5 | 70.8 | 8.2 | 9.1 | 3 | 8.3 | 7 | 19.4 | 21 | 79.2 |

The preferred cholesterol-rich fraction can be prepared by an alternate process described in the following example.

EXAMPLE 5

Fresh bovine serum was brought to a temperature of 20°–25° C. and 14.7 g/l of sodium citrate (serum ionic strength of 0.5) was added. The resulting solution was agitated for at least 30 minutes, and the pH was adjusted to 6.9–7.1 by addition of appropriate amount of 1N sodium hydroxide or 1N hydrochloric acid. Finely-divided silica was added in an amount of 10 g/l, and the resulting slurry was agitated for 3–4 hours at room temperature. Polyethylene glycol having nominal molecular weight of 3350 daltons was added in an amount of 10 g/l, and the resulting mixture was agitated for 1 hour at room temperature. The silica containing adsorbed material was then separated from the liquid phase by centrifugation, and the liquid was discarded. The silica paste was then frozen at −20° C. and stored at that temperature for at least 2 weeks. The frozen paste was then thawed at room temperature for 24–48 hours until no visible ice crystals were present. The expressed liquid was discarded. The silica paste was then suspended in 2 liters of 0.85 percent (weight/volume basis) aqueous sodium chloride solution (0.146M NaCl) for each kilogram of silica paste. It was mixed gently for 15 minutes and allowed to settle for at least 3 hours for adequate sedimentation. The supernatant liquid was siphoned off and discarded. This washing step was repeated at least two times. The washed paste was then suspended in 2 liters deionized water per kilogram of silica paste with agitation at room temperature. The resulting suspension was then carefully warmed to 20°–25° C. The pH was adjusted to 10.5 with addition of 1N sodium hydroxide. The resulting suspension was stirred at room temperature for 2 hours while constantly maintaining pH at 10.4–10.6 by addition of 1N sodium hydroxide or hydrochloric acid. The stirring was stopped, and the suspension was allowed to settle for at least 12 hours. The supernatant was removed by siphon and clarified by filtration and centrifugation. The silica was discarded. The liquid was then frozen at −20° C. and stored at that temperature for 48–72 hours. The frozen material was then thawed at room temperature for 48–72 hours until no visible ice crystals were present. The resulting liquid product was clarified by centrifugation and any solid material was discarded. The pH of the clarified solution was adjusted to 11.9–12.1 by addition of 1N sodium hydroxide. The solution was then concentrated to about 20–25 percent of its initial volume by ultrafiltration using hollow fiber or spiral wound molecular filters having a nominal molecular weight cut-off of 5,000–30,000 daltons. The concentrated material was then dialyzed against 7 volumes of 0.3 M sodium carbonate and against 7 volumes of deionized water. The solution was then concentrated by ultrafiltration to its volume prior to dialysis. The pH was then adjusted to 8.6 by addition of 1N hydrochloric acid, and the resulting solution was heated at 80° C. for at least 30 minutes. The solution was then cooled to about 30° C. The cholesterol level of the product was analyzed by known techniques and diluted to a concentration of 10 mg./ml with deionized water. Sodium chloride in an amount of 8.5 g/l was then added and the pH was adjusted to 7.7–7.9 by addition of 1N sodium hydroxide or hydrochloric acid. The resulting product was then sterile filtered using 0.45 and 0.2 micron microporous filtration media. The filtered materials was then recovered as a purified cholesterol-rich fraction.

This product material can be used in the same manner as that described above in Examples 1–4.

What is claimed is:

1. A process for the growth of *Treponema hyodysenteriae* in an appropriate nutrient medium for subsequent use of the resulting cells in a bacterin, which comprises growing *Treponema hyodysenteriae* in a nutrient medium containing a cholesterol-rich bovine fraction obtained from bovine plasma or serum wherein the cholesterol-rich bovine fraction is prepared by a process comprising the steps of:

(a) contacting a liquid cholesterol-containing bovine plasma or serum with a silica adsorbent to adsorb the cholesterol-rich fraction;

(b) separating the adsorbed cholesterol-rich fraction from the remaining liquid plasma or serum;

(c) freezing and thawing the adsorbed cholesterol-rich fraction;

(d) eluting the adsorbed cholesterol-rich fraction at a pH from 9.0 to 11.5;

(e) either before or after step (f) and prior to step (g) adjusting the pH of the cholesterol-rich solution to a value in the range from 11.0 to 13.0;

(f) concentrating the cholesterol-rich solution by ultrafiltration;

(g) dialyzing the concentrated cholesterol-rich solution sequentially against sodium carbonate and water;

(h) further concentrating the dialyzed cholesterol-rich solution by ultrafiltration;

(i) adjusting the pH of the concentrated cholesterol-rich solution to a value in the range from 7.0 to 11.0;

(j) heating the concentrated cholesterol-rich solution at 50° to 100° C. for 30 minutes to 24 hours;

(k) recovering therefrom a purified cholesterol-rich fraction.

2. A process according to claim 1 wherein the nutrient medium contains from 0.1 to 5.0 volume percent cholesterol-rich bovine fraction.

3. A process according to claim 1 wherein the nutrient medium contains from 1 to 2.5 volume percent of a cholesterol-rich bovine fraction prepared by a process comprising the steps of:

(a) contacting a liquid cholesterol-containing bovine serum or plasma with a silica adsorbent to adsorb the cholesterol-rich fraction;
(b) separating the adsorbed cholesterol-rich fraction from the remaining liquid serum or plasma;
(c) freezing and thawing the adsorbed cholesterol-rich fraction;
(d) eluting the adsorbed cholesterol-rich fraction at a pH from 10.4 to 10.6;
(e) freezing and thawing the eluted cholesterol-rich fraction;
(f) adjusting the pH of the cholesterol-rich fraction to a value of 12.0;
(g) concentrating the cholesterol-rich fraction by ultrafiltration to a volume from 15 to 50 percent of the starting volume;
(h) dialyzing the concentrated cholesterol-rich fraction sequentially against sodium carbonate and water;
(i) further concentrating the dialyzed cholesterol-rich fraction by ultrafiltration to the volume it had at the beginning of step (h);
(j) adjusting the pH of the concentrated cholesterol-rich fraction to a value of 8.6;
(k) heating the concentrated cholesterol-rich fraction at 80° C. for 30 minutes to 5 hours;
(l) recovering therefrom a purified cholesterol-rich fraction.

* * * * *